(12) United States Patent
Harris (10) Patent No.: US 10,772,757 B1
(45) Date of Patent: Sep. 15, 2020

(54) ANTI-SNORING MOUTH GUARD

(71) Applicant: Chad Harris, Du Quoin, IL (US)

(72) Inventor: Chad Harris, Du Quoin, IL (US)

( * ) Notice: Subject to any disclaimer, the term of this patent is extended or adjusted under 35 U.S.C. 154(b) by 0 days.

(21) Appl. No.: 16/678,422

(22) Filed: Nov. 8, 2019

Related U.S. Application Data (60) Provisional application No. 62/862,912, filed on Jun. 18, 2019.

(51) Int. Cl.
*A61F 5/56* (2006.01)

(52) U.S. Cl.
CPC ............ *A61F 5/566* (2013.01); *A61F 5/56* (2013.01)

(58) Field of Classification Search
CPC ....... A61F 5/56; A61F 5/566; A61M 16/0488; A61M 16/049; A61M 16/0493; A61M 16/0495
USPC ......................................... 128/848, 860–862
See application file for complete search history.

(56) References Cited

U.S. PATENT DOCUMENTS

| 6,041,784 | A | * | 3/2000 | Halstrom | ............... | A61F 5/566 128/848 |
| 8,739,794 | B2 | * | 6/2014 | Cutler | ............... | A61F 5/566 128/207.14 |
| 2018/0200103 | A1 | * | 7/2018 | Keropian | ............... | A61F 5/566 |

* cited by examiner

*Primary Examiner* — Keri J Nelson
(74) *Attorney, Agent, or Firm* — Dale J. Ream (57) ABSTRACT

An anti-snoring mouth guard for insertion into a mouth of a user for decreasing snoring and the effects of sleep apnea includes a mouthpiece portion having a bottom wall and a pair of upstanding side walls displaced and opposite one another and extending upwardly from the bottom wall, said mouthpiece having a hemispherical configuration that is complementary to a shape of the user's teeth. Collectively, the bottom wall and pair of side walls define a channel operable to receive teeth of a user's upper pallet. The anti-snoring mouth guard includes tongue depressor portion having a proximal end coupled to the mouthpiece and having a body extending rearwardly at a generally downward angle. A brace may extend between rear ends of the mouthpiece portion and define levels by which the tongue depressor may be inserted such that the tongue depressor may be adjusted vertically and front-to-back.

10 Claims, 6 Drawing Sheets

ANTI-SNORING MOUTH GUARD

REFERENCE TO RELATED APPLICATIONS

This application claims the priority of provisional patent application U.S. Ser. No. 62/862,912 filed Jun. 18, 2019 titled Anti-Snoring Mouth Guard and which is incorporated in its entirety herein by reference.

BACKGROUND OF THE INVENTION

This invention relates generally to anti-snoring devices and, more particularly, to a mouthpiece for insertion into a person's mouth having a tongue depressor that suppresses or prevents the person's tongue from impeding his airway and, as a result, reducing or eliminating snoring and obstructive apnea.

Snoring is often perceived merely as "noisy breathing" when sleeping. Snoring happens when you can't move air freely through your nose and throat during sleep. However, snoring may actually be much more of a health concern, such as heart disease or another breathing dysfunction. About one-half of people who snore loudly have obstructive sleep apnea. Sleep apnea is a potentially serious sleep disorder in which breathing repeatedly stops and starts. Persons with sleep apnea often wear a CPAP mask for years to prevent the negative effects of sleep apnea, including possible death. Prevention of obstructive snoring, then, is of prime interest to persons with dangerous snoring and sleep apnea.

Various devices have been proposed for decreasing or preventing snoring. Although presumably effective for their intended purposes, there is still a need for a lightweight and simple solution for preventing a person's tongue from obstructing the person's airway and allowing snoring to occur.

Therefore, it would be desirable to have a mouth guard for insertion into a mouth of a user for decreasing snoring and the effects of sleep apnea. Further, it would be desirable to have a mouth guard for insertion into a mouth of a snorer having a tongue depressor portion that is adjustable vertically, longitudinally, and angularly.

SUMMARY OF THE INVENTION

An anti-snoring mouth guard for insertion into a mouth of a user for decreasing snoring and the effects of sleep apnea according to the present invention includes a mouthpiece portion having a bottom wall and a pair of upstanding side walls displaced and opposite one another and extending upwardly from the bottom wall, the mouthpiece having a hemispherical configuration that is complementary to a shape of the user's teeth. Collectively, the bottom wall and pair of side walls define a channel operable to receive teeth of a user's upper pallet. The anti-snoring mouth guard includes a proximal end coupled to the mouthpiece and having a body extending rearwardly at a generally downward angle. The tongue depressor portion may include adjustment structures so as to adjustable vertically, front-to-back, presumably by a dentist or dental technician.

Therefore, a general object of this invention is to provide a mouth guard receivable on the upper pallet of a user's teeth and operable to hold a user's tongue so as to decrease snoring and the affects of sleep apnea.

Another object of this invention is to provide a mouth guard, as aforesaid, in which a tongue depressor portion is vertically adjustable relative to the mouthpiece portion.

Still another object of this invention is to provide a mouth guard, as aforesaid, in which a tongue depressor portion is longitudinally (frontwardly and rearwardly) adjustable relative to the mouthpiece portion.

Yet another object of this invention is to provide a mouth guard, as aforesaid, that can inhibit or stop snoring with a mouthpiece for only the upper pallet of a person's mouth.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 2a is a side view of the anti-snoring mouth guard as in FIG. 1a;

FIG. 2b is a rear view of the anti-snoring mouth guard as in FIG. 1a;

FIG. 3b is an exploded view of the anti-snoring mouth guard as in FIG. 3a;

FIG. 4b is an exploded view of the anti-snoring mouth guard as in FIG. 4a;

FIG. 6a is an exploded view of the anti-snoring mouth guard as in FIG. 5a; and

FIG. 6b is an isolated view on an enlarged scale taken from FIG. 6a.

DESCRIPTION OF THE PREFERRED EMBODIMENT

An anti-snoring mouth guard according to a preferred embodiment of the present invention will now be described with reference to FIGS. 1a to 6b of the accompanying drawings. The anti-snoring mouth guard 10 may include a mouthpiece portion 20 and tongue depressor portion 30 coupled to the mouthpiece.

With regard to FIG. 1a to 3b, the mouthpiece portion 20 of the anti-snoring mouth guard 10 may include a bottom wall 22 and a pair of upstanding side walls, referred to generally with reference numeral 24 and specifically as a pair of side walls 24a and 24b, extending upwardly from the bottom wall 22. The side walls 24 are displaced from one another and are parallel to one another. Collectively, the bottom wall 22 and pair of side walls 24a, 24b define an interior area, such as a channel or trough operable to selectively receive the teeth of a person's upper pallet. In other words, the mouthpiece portion 20 has a generally hemispherical configuration complementary to a user's upper teeth and can be inserted comfortably into a user's mouth, such as at night. It is understood that the side walls 24 include an inner side wall 24a and an outer side wall 24b, each having interior surfaces facing one another that may be contoured or define recesses operable to receive associated teeth in nested relationships, respectively. The front or apex of the mouthpiece portion 20 may be referred to as a front section 28. By contrast, the pair of side walls 24a, 24b extends away from the apex rearwardly to terminal ends, respectively, and which will be referred to as rear ends 29 of the mouthpiece 20. As shown, the rear ends 29 have an open configuration as the exact number and size of a patient's teeth will not be known at a point of manufacturing.

The mouthpiece portion 20 includes a support brace 26 adjacent at least one rear end 29 of the mouthpiece. In one embodiment, the support brace 26 may be positioned along an inner surface of the inner side wall 24a of the pair of side walls 24a, 24b and will be discussed in more detail later. Preferably, however, the support brace 26 extends between respective rear ends 29 of the pair of side walls (or, more particularly, from rear ends of the inner side wall 24) and may be referred to as a bridge—also using reference numeral 26'.

Further, the tongue depressor portion 30 of the anti-snoring tongue guard 10 includes a proximal end 32 coupled to the bridge 26 of the mouthpiece portion 20 and includes a body 34 extending from the proximal end 32. Preferably, the proximal end 32 is coupled to the mouthpiece side of the bridge 26 and the body 34 curves around (i.e. under) the bridge 26 such that the proximal end and body may have a generally U-shaped configuration. The proximal end 32 of the body 34 of the tongue depressor portion 30 may have a width that is the same or complementary to the distance between interior surfaces of respective interior side walls of the mouthpiece. In other words, the proximal end 32 of the tongue depressor portion 30 may extend completely between peripheral walls of the mouthpiece portion 20. The body 34 of the tongue depressor portion 30 extends rearwardly from the proximal end 32 at a generally downward angle so as to bear against a user's tongue when the mouthpiece portion 20' is inserted into the user's mouth. The tongue depressor portion 30 may include a distal end 36 opposite the proximal end 32 and extending away from the body 34.

In another aspect, the tongue depressor portion 30 may be movable front-to-rear (longitudinally) and also upwardly-downwardly (e.g. vertically) relative to the mouthpiece portion 20, as will be described below and is illustrated in FIGS. 1a to 3b In general, the bridge 26 may define one or more slots and the proximal end 32 of the tongue depressor portion may include one or more flanges 38 configured for insertion into respective slots, each of the slots and flanges having a plurality of flange openings and apertures adjacent one another and arranged in a longitudinal pattern, respective slot and flange combinations being in registration or alignment with one another. More particularly, the bridge 26 may define a first slot 40 (also referred to as an upper slot), the bridge also defining a plurality of apertures (i.e. first apertures 41) in communication with the first slot 40. In the illustrations, three apertures are illustrated although more or fewer apertures are contemplated) adjacent one another in a longitudinally (front to back) extending line. Similarly, the bridge 26 may define a second slot 42 vertically adjacent to but separated from the first slot 40, the bridge also defining a plurality of apertures (i.e. second apertures 43) in communication with the second slot 42. Further, the bridge 26 may define a third slot 44 vertically adjacent to but separated from the second slot 42, the bridge also defining a plurality of apertures (i.e. third apertures 45) in communication with the third slot 44. In other words, the bridge 26 may define at least three vertical levels of slots and each slot is in communication with multiple apertures arranged longitudinally front-to-back relative to the mouthpiece portion 20.

Figure 1A:
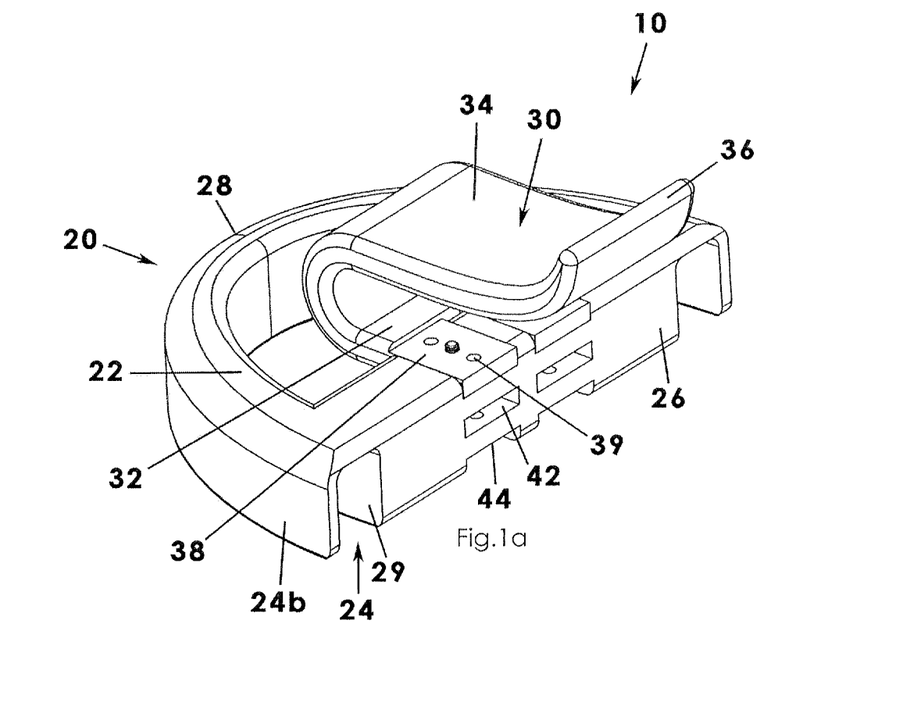
FIG. 1a is a perspective view of an anti-snoring mouth guard according to an embodiment of the present invention, illustrated in an inverted configuration for clarity.
Figure 1B:
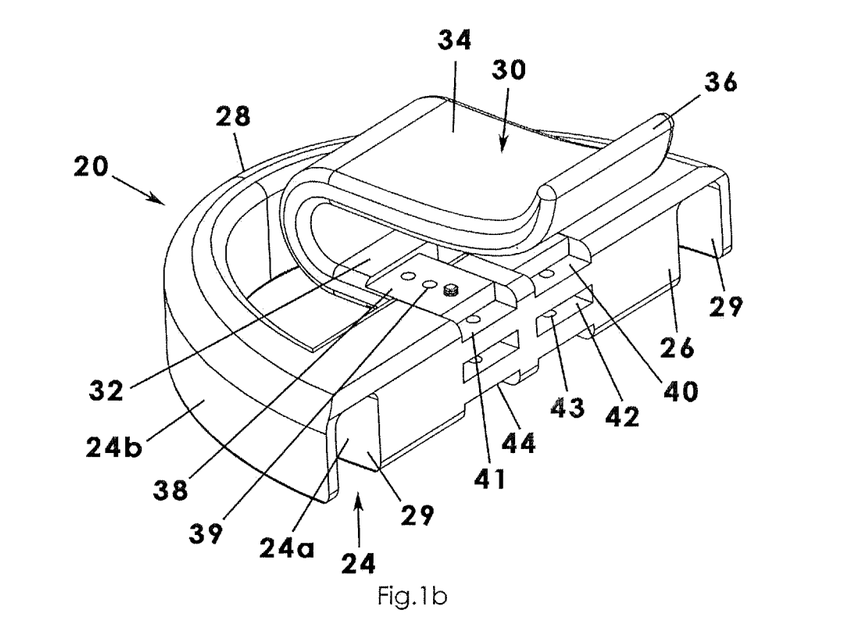
FIG. 1b is another perspective view of the anti-snoring mouth guard as in FIG. 1a, illustrated with the tongue depressor portion in another front-back setting.
Figure 2A:
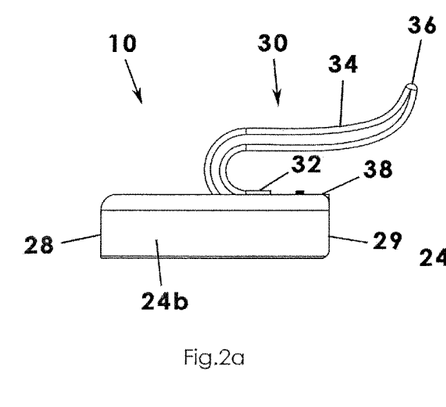
Figure 2B:
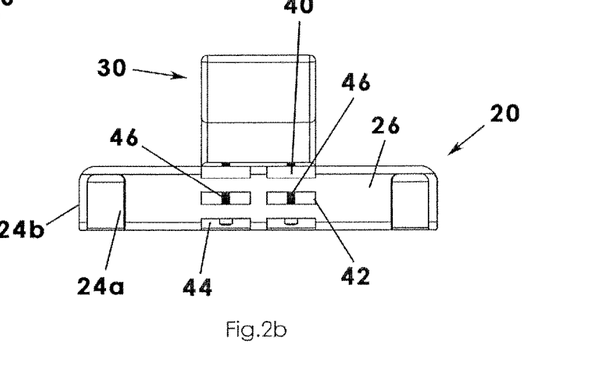
Figure 3A:
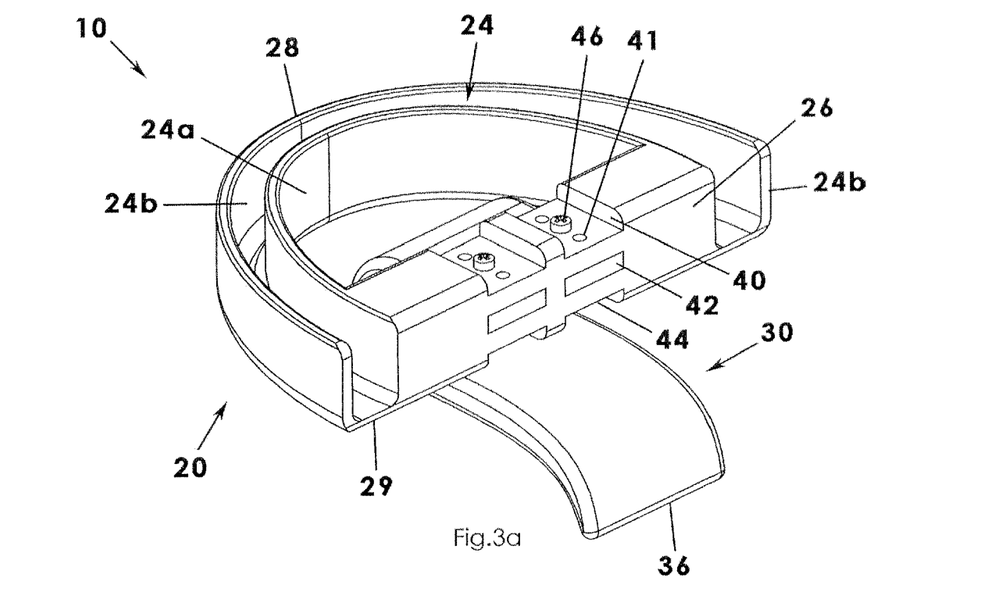
FIG. 3a is a perspective view of the anti-snoring mouth guard as in FIG. 1a in a face up configuration and illustrating another height level configuration.
Figure 3B:
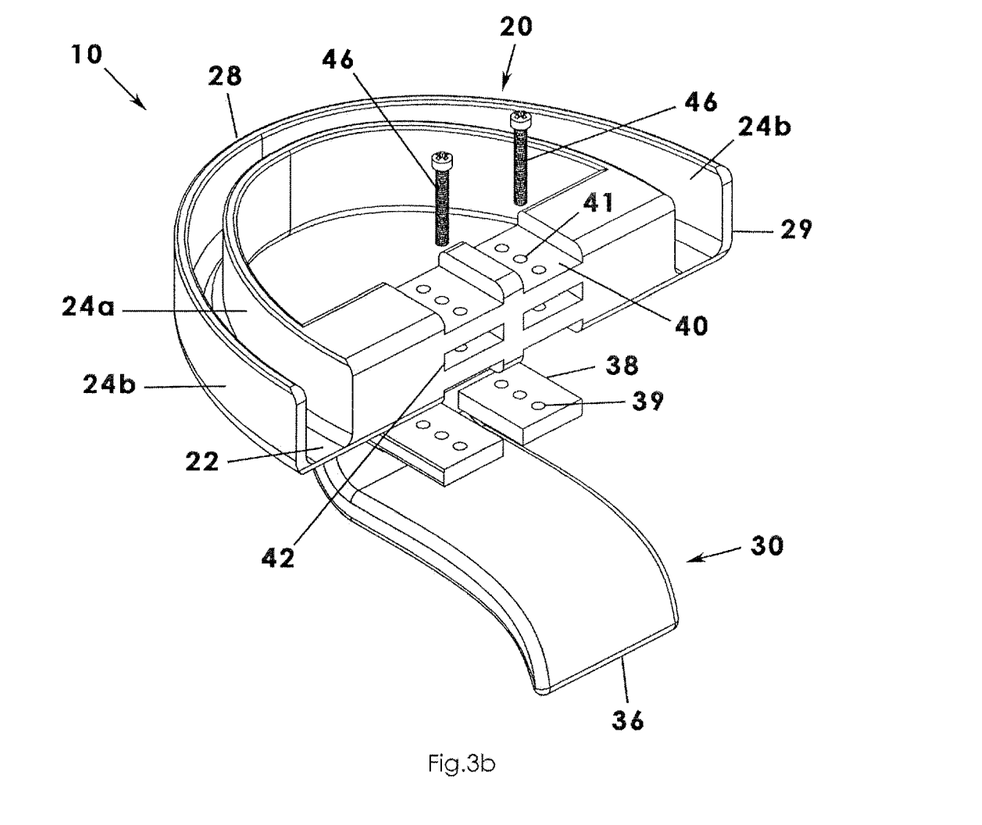

Further to the construction described immediately above, at least one flange 38 is coupled to and extends away from the proximal end 32 of the tongue depressor portion 30. The flange 38 may have a planar configuration complementary to a planar configuration of a respective slot. In this embodiment, the flange 38 extends rearwardly from the proximal end 32 (FIG. 1b). The flange 38 defines a plurality of flange openings 39 corresponding to the plurality of apertures of each slot level, respectively. As will be described below, selected apertures and flange openings may be aligned so that the flange 38 and mouthpiece portion 20 may be coupled together with a fastener 46 inserted through a selected aperture and flange opening. It will be understood and as shown in the drawings, each slot may include a left slot and a right slot; similarly, the flange 38 may include a left flange and a right flange so as to enhance the strength and alignment of the tongue depressor portion 30. The left and right flanges may be referred to as a pair of flanges. The left and right slot may be referred to as a pair of left slots or right slots, respectively.

As described, the bridge 26 may appear to be a three-level or three tiered shelf system into which a flange 38 may be inserted and coupled so as to vertically adjust a position of the tongue depressor portion 30. To adjust the tongue depressor portion 30 vertically, the flange (or flanges) are inserted into the first slot 40, the second slot 42, or the third slot 44. The slots may also be described as upper, middle, and lower slots. Then, to adjust the tongue depressor portion 30 forwardly or rearwardly within a selected level, the entire tongue depressor portion 30 is moved forwardly or rearwardly until the desired apertures and openings are aligned. Then, the respective flange 38 and bridge 26 are coupled together by inserting one or more fasteners 46 (e.g. dental screws) through aligned apertures and openings. It will be understood that the precise configuration and adjustment of the anti-snoring mouth guard 10 may be determined and assembled by a dentist or dental technician, such as during a dental visit and the determined specification may then be outsourced to a lab or manufacturer to generate the anti-snoring mouth guard for a patient in a manner similar to eyeglass lenses.

Figure 4A:
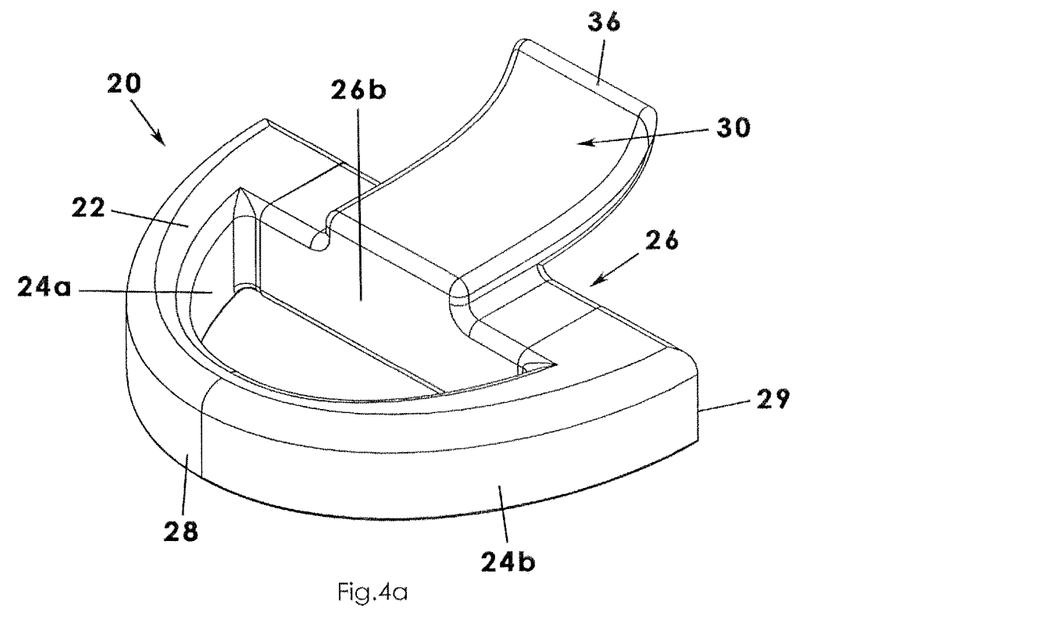
FIG. 4a is a perspective view of the anti-snoring mouth guard according to the present invention illustrating a variation on the vertical and front-rear movement structure.
Figure 4B:
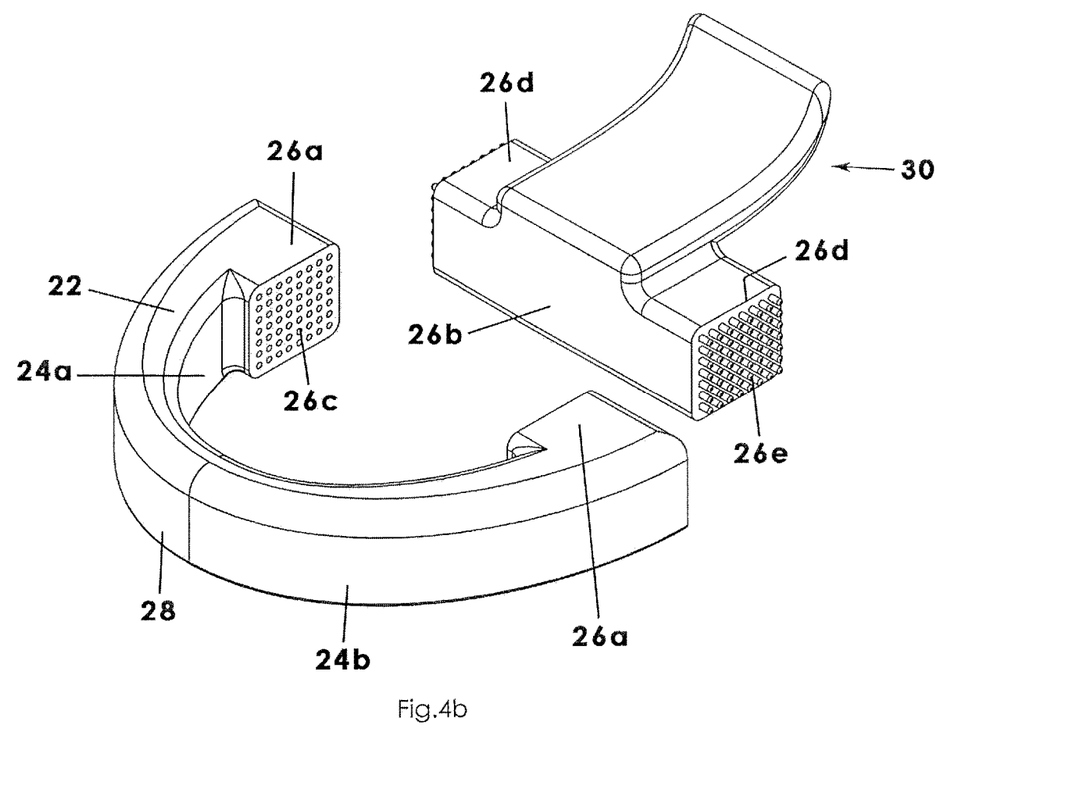

As an alternative to the support brace 26 extending entirely between rear ends 29 of the pair of side walls, the support brace 26 may include truncated end portions 26a defining a plurality of apertures 26c respectively (FIGS. 4a and 4b). Similarly, a body 26b of the support brace 26 (or bridge) includes a pair of opposed ends 26d each having a plurality of prongs 26e extending away therefrom and arranged in one or more rows. Accordingly, a user, such as a dentist, is able to align selected apertures and prongs of the support brace 26 to adjust the position of the tongue depressor portion 30 vertically and longitudinally (front to back) relative to the mouthpiece portion 20. In an embodiment, respective prongs and apertures may be held in a selected position in a friction fits configuration, with dental cement, with a fastener, or the like.

Another embodiment of the present invention will be described with reference to FIGS. 5a to 6b, is substantially similar in its construction to the embodiment first described except as specifically noted, and primed reference numerals will be used for substantially similar structures as those described previously. With regard to FIG. 5a to 5b, the mouthpiece portion 20' of the anti-snoring mouth guard 10' may include a bottom wall 22' and a pair of upstanding side walls 24' extending upwardly from the bottom wall 22'. The side walls 24' are displaced from one another and are parallel to one another. Collectively, the bottom wall 22' and pair of side walls 24' define an interior area, such as a channel or trough operable to selectively receive the teeth of a person's upper pallet. In other words, the mouthpiece portion 20' has a generally hemispherical configuration complementary to a user's upper teeth and can be inserted comfortably into a user's mouth, such as at night. It is understood that the side walls 24' include an inner side wall and an outer side wall 24b', each having interior surfaces facing one another that may be contoured or define recesses operable to receive associated teeth in nested relationships, respectively. The front or apex of the mouthpiece portion 20' may be referred to as a front section 28'. By contrast, the pair of side walls 24' extends away from the apex rearwardly to terminal ends, respectively, and which will be referred to as rear ends 29' of the mouthpiece 20'. As shown, the rear ends 29' have an open configuration as the exact number and size of a patient's teeth will not be known at a point of manufacturing.

Figure 5A:
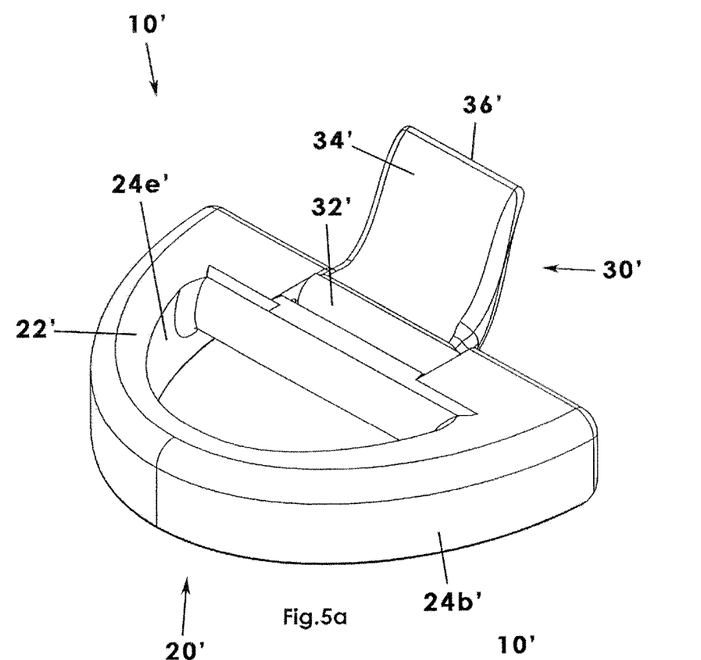
FIG. 5a is a perspective view of an anti-snoring mouth guard according to an embodiment of the present invention, illustrated with the tongue depressor portion in one angled configuration.
Figure 5B:
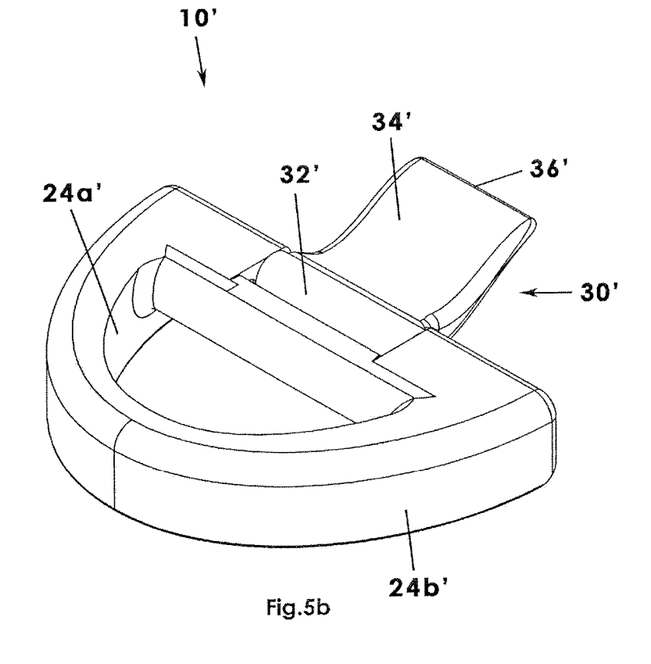
FIG. 5b is a perspective view of the anti-snoring mouth guard as in a modified angled configuration.
Figure 6A:
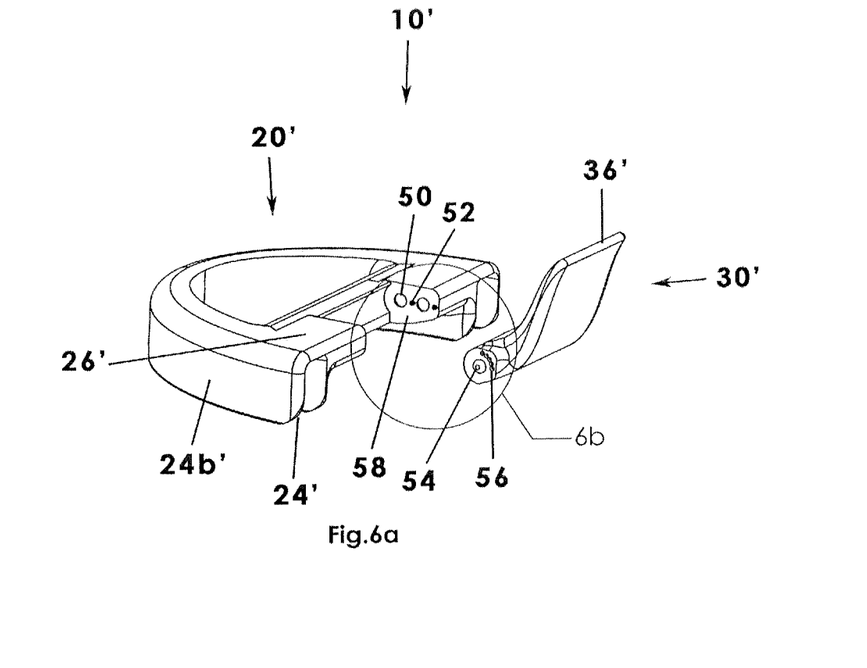
Figure 6B:
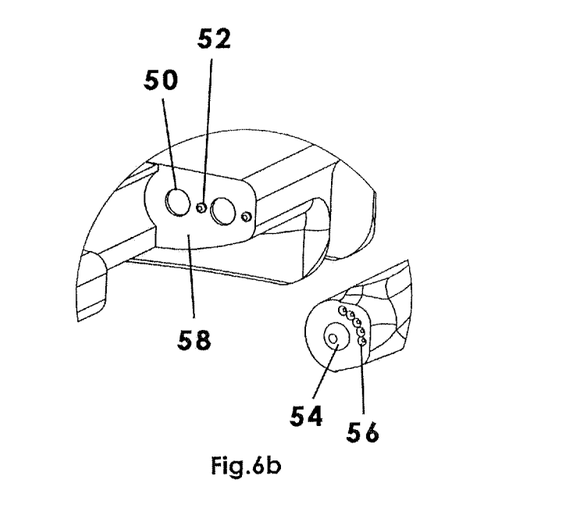

The mouthpiece portion 20' includes a support brace 26' adjacent at least one rear end 29' of the mouthpiece. In one embodiment, the support brace 26' may be positioned along an inner surface of the inner side wall 25' of the pair of side walls and will be discussed in more detail later. Preferably, however, the support brace 26' extends between respective rear ends 29' of the pair of side walls (or, more particularly, from rear ends of the inner side wall 24') and may be referred to as a bridge—also using reference numeral 26'.

Further, the tongue depressor portion 30' of the anti-snoring tongue guard 10' includes a proximal end 32' coupled to the bridge 26' of the mouthpiece portion 20' and includes a body 34' extending from the proximal end 32'. Preferably, the proximal end 32' is coupled to the mouthpiece side of the bridge 26' and the body 34' curves around (i.e. under) the bridge 26' such that the proximal end and body may have a generally U-shaped configuration. The proximal end 32' of the body 34' of the tongue depressor portion 30' may have a width that is the same or complementary to the distance between interior surfaces of respective interior side walls of the mouthpiece. In other words, the proximal end 34' of the tongue depressor portion 30' may extend completely between peripheral walls of the mouthpiece portion 20'. The body 34' of the tongue depressor portion 30' extends rearwardly from the proximal end 32' at a generally downward angle so as to bear against a user's tongue when the mouthpiece portion 20' is inserted into the user's mouth. The tongue depressor portion 30' may include a distal end 36' opposite the proximal end 32' and extending away from the body 34'.

It is also contemplated that the tongue depressor portion 30 may be adjusted angularly via an angle adjustment assembly. In an embodiment shown in FIGS. 5a to 6b, the tongue depressor portion 30' may be hingedly or pivotally coupled to the mouthpiece portion 20'. More particularly, the forward end 32' of the tongue depressor portion 30' may be pivotally coupled to the body 34' and may be operably configured to enable a user to adjust and determine the angle the distal member 36' extends downwardly against the tongue. The tongue depressor portion 30' and mouthpiece portion 20' may include an adjustment assembly having structure enabling selective angling of the tongue depressor portion 30'. In an embodiment, the adjustment assembly may include a nub and a plurality of recesses (FIG. 6b) or other selectable position construction. Specifically, the support member 26' may include a truncated section or cutout section having a pair of inward and opposite facing walls (referred as inward walls 58) each defining a pair of pivot sockets 50 and having a locking nub 52. Each pivot socket 50 may extend inwardly and each locking nub 52 may extend outwardly. Then, in complementary fashion, opposed sides of the forward end 32' of the tongue depressor portion 30' may include a pivot boss 54 dimensioned for receipt by a respective pivot socket 50 and may include a plurality of position locking recesses 56 adjacent the a respective pivot socket and dimensioned and operable to selectively mate with a respective locking nub 52. It is understood that the recesses are not deep but rather adjustments are made by a user overcoming a mild friction fit therebetween. It is also understood that which of the adjustment components are inwardly shaped or outwardly shaped can be reversed in another embodiment and still be included in the spirit of the present disclosure. In use, a respective pivot socket 50 receives a respective pivot boss 54 and a user is able to pivot the tongue depressor portion 30 to a selected and desired angle where the locking nub 52 may be received (and removably locked) into a selected position locking recess 46. In other words, the user is able to select how much or how little pressure is put on his tongue while sleeping.

Although a mouthpiece portion only involving receiving the upper teeth of a user's mouth is preferred, a mouthpiece portion designed to receive both upper and lower teeth is within the spirit of the present disclosure.

In use, a person may be fitted for a custom-built mouth guard by his or her dentist or technician. Preferably, the mouthpiece portion 20 is formed according to a scan or mold taken of the user's upper pallet of teeth. Then, the tongue depressor portion 30 may be adjusted according to the size and shape of the patient's tongue and mouth cavity, the elevation, forward, and rearward position being adjustable as described above.

Accordingly, a person simply inserts the mouth guard 10 into his mouth at bedtime and snoring is reduced. No longer is a CPAP machine needed as the mouth guard 10 prevents the user's tongue from rearward movement that closes the airway and causes snoring.

It is understood that while certain forms of this invention have been illustrated and described, it is not limited thereto except insofar as such limitations are included in the following claims and allowable functional equivalents thereof.

The invention claimed is:

1. An anti-snoring mouth guard for insertion into a mouth of a user, comprising:
    a mouthpiece portion having a bottom wall and a pair of side walls opposite and parallel to one another and extending upwardly from the bottom wall so as to define a channel having a hemispherical configuration complementary to a shape of the user's teeth;
    wherein said pair of side walls have are continuous walls, respectively, and a pair of rear ends that are terminal and that are open;
    a brace extending between said rear ends of said mouthpiece portion; and
    a tongue depressor portion having a proximal end coupled to said mouthpiece portion adjacent said rear ends, said tongue depressor portion having a body coupled to said proximal end and that extends rearwardly away from said rear ends of said mouthpiece portion and at a downward angle;

wherein said tongue depressor portion includes a flange coupled to and extending away from said proximal end, said flange defining a plurality of flange openings;

said brace defines a first slot and defines a plurality of first apertures in communication with said first slot; and said flange, when positioned in said first slot such that said plurality of flange openings are aligned with said plurality of first apertures, is coupled to said brace by a fastener inserted through a selected one of said plurality of first apertures and a selected one of said plurality of flange openings, respectively;

said brace defines a second slot vertically adjacent to said first slot, said brace defining a plurality of second apertures in communication with said second slot; and said flange, when positioned in said second slot such that said plurality of flange openings are aligned with said plurality of second apertures, is coupled to said brace by said fastener inserted through said selected one of said plurality of second apertures and said selected one of said plurality of flange openings, respectively.

2. The anti-snoring mouth guard as in claim 1, further comprising means for moving said tongue depressor portion forwardly and rearwardly relative to said mouthpiece portion.

3. The anti-snoring mouth guard as in claim 2, further comprising means for moving said tongue depressor portion vertically relative to said mouthpiece portion.

4. The anti-snoring mouth guard as in claim 1, wherein:
said brace defines a third slot vertically adjacent to said second slot, said brace defining a plurality of third apertures in communication with said third slot; and said flange, when positioned in said third slot such that said plurality of flange openings are aligned with said plurality of third apertures, is coupled to said brace by said fastener inserted through a selected one of said plurality of third apertures and said selected one of said plurality of flange openings, respectively.

5. The anti-snoring mouth guard as in claim 4, wherein:
said flange includes a pair of flanges that are laterally spaced apart and adjacent one another;

said first slot includes a pair of first slots that are laterally spaced apart and adjacent one another and configured to receive said pair of flanges, respectively;

said second slot includes a pair of second slots that are laterally spaced apart and adjacent one another and configured to receive said pair of flanges, respectively; and said third slot includes a pair of third slots that are laterally spaced apart and adjacent one another and configured to receive said pair of flanges, respectively.

6. The anti-snoring mouth guard as in claim 4, wherein said fastener is a dental screw.

7. An anti-snoring mouth guard for insertion into a mouth of a user, comprising:
a mouthpiece portion having a bottom wall and a pair of side walls extending upwardly from the bottom wall so as to define a channel having a hemispherical configuration complementary to a shape of an upper pallet of the user's teeth;

wherein said pair of side walls include an outer wall and an inner wall extending parallel to said outer wall, said pair of side walls terminating at rear ends of said mouthpiece, respectively, said rear ends being displaced from one another and having open configurations;

a brace extending between said rear ends of said mouthpiece portion;

a tongue depressor portion having a proximal end coupled to said mouthpiece portion adjacent said rear ends, said tongue depressor portion having a body coupled to said proximal end and that extends rearwardly away from said rear ends of said mouthpiece portion and at a predetermined angle to said mouthpiece portion;

wherein said tongue depressor portion includes a flange coupled to and extending away from said proximal end, said flange defining a plurality of flange openings;

wherein:
said brace defines a first slot and defines a plurality of first apertures in communication with said first slot; and said flange, when positioned in said first slot such that said plurality of flange openings are aligned with said plurality of first apertures, is coupled to said brace by a fastener inserted through a selected one of said plurality of first apertures and a selected one of said plurality of flange openings, respectively;

said brace defines a second slot vertically adjacent to said first slot, said brace defining a plurality of second apertures in communication with said second slot; and said flange, when positioned in said second slot such that said plurality of flange openings are aligned with said plurality of second apertures, is coupled to said brace by said fastener inserted through said selected one of said plurality of second apertures and said selected one of said plurality of flange openings, respectively.

8. The anti-snoring mouth guard as in claim 7, wherein:
said brace defines a third slot vertically adjacent to said second slot, said brace defining a plurality of third apertures in communication with said third slot; and said flange, when positioned in said third slot such that said plurality of flange openings are aligned with said plurality of third apertures, is coupled to said brace by said fastener inserted through a selected one of said plurality of third apertures and said selected one of said plurality of flange openings, respectively.

9. The anti-snoring mouth guard as in claim 8, wherein:
said flange includes a pair of flanges that are laterally spaced apart and adjacent one another;

said first slot includes a pair of first slots that are laterally spaced apart and adjacent one another and configured to receive said pair of flanges, respectively;

said second slot includes a pair of second slots that are laterally spaced apart and adjacent one another and configured to receive said pair of flanges, respectively; and said third slot includes a pair of third slots that are laterally spaced apart and adjacent one another and configured to receive said pair of flanges, respectively.

10. The anti-snoring mouth guard as in claim 7, wherein said fastener is a dental screw.

* * * * *